United States Patent [19]
White et al.

[11] Patent Number: 5,985,261
[45] Date of Patent: Nov. 16, 1999

[54] USE OF THIOREDOXIN-LIKE MOLECULES FOR INDUCTION OF MNSOD TO TREAT OXIDATIVE DAMAGE

[75] Inventors: Carl W. White, Denver; Kumuda C. Das, Aurora, both of Colo.

[73] Assignee: National Jewish Medical and Research Center, Denver, Colo.

[21] Appl. No.: 08/883,804

[22] Filed: Jun. 27, 1997

Related U.S. Application Data

[60] Provisional application No. 60/020,740, Jun. 28, 1996.

[51] Int. Cl.$^6$ .......................... A61K 45/05; A61K 38/00; C07K 13/00
[52] U.S. Cl. ...................... 424/85.1; 424/85.2; 424/450; 514/2; 514/12; 514/17; 514/18; 514/824; 514/826; 514/886; 530/329; 530/330; 530/399
[58] Field of Search ................................ 424/85.1, 85.2, 424/450; 514/2, 12, 17, 18, 824, 826, 886; 530/329, 330, 399

[56] References Cited

U.S. PATENT DOCUMENTS

| | | | |
|---|---|---|---|
| 4,771,036 | 9/1988 | Pigiet et al. | 514/12 |
| 5,210,073 | 5/1993 | Yodoi et al. | 514/17 |

FOREIGN PATENT DOCUMENTS

| | | |
|---|---|---|
| 5310579 | 11/1993 | Japan . |
| WO 91/04320 | 4/1991 | WIPO . |
| WO 95/16044 | 6/1995 | WIPO . |

OTHER PUBLICATIONS

Temmesfeld–Wollbruck et al, *Lung*, vol. 173, No. 3, pp. 139–164, 1995.
Das et al., *Am. J. Physiol.* (Lung Cell. Mol. Physiol. 13): L588–L602, 1995.
Fukuse et al, *Thorax*, vol. 50, pp. 387–391, 1995.
Van Asbeck et al, *Resuscitation.*, 18, Suppl. S63–S83, 1989.
Buchanan et al. *Archives of Biochemistry and Biophysics*, vol. 314, No. 2, pp. 257–260, 1994.
Sato et al, (*Methods in Enzymology*), vol. 252, pp. 343–348, 1995.
Wada et al, *Eur. Sur. Res.*, vol. 27, No. 6, pp. 363–370, 1995.
Hawkins et al, *Pharmacology Biochemistry and Behavior*, vol. 52, No. 3, pp. 509–515, 1995.
Bernard, 1991, *Am J. Med.*, 91(3C):54S–59S, Abstract.
Christman et al., 1993, *New Horiz*, 1(4):623–30, Abstract.
Das et al., 1995, *Molecular and Cellular Biochemistry*, 148:45–57.
Das et al., 1995, *Oxgen '95*, 2nd Annual Meeting of the Oxygen Society, Abstract Form.
Flaherty et al., 1988, *Free Radical Biology & Medicine*, 5:409–419.
Fujii et al., 1991, *Virchows Archiv A Pathol. Anat.*, 419:317–326.
Goto et al., 1992, *Free Radical Biology & Medicine*, 13:47–53.
Holmgren, 1979, *The Journal of Biological Chemistry*, 254(18):9113–9119.
Holmgren, 1989, *The Journal of Biological Chemistry*, 264(24):13963–13966.
Housset, 1994, *CR Seances Soc Biol Fil*, 188(4):321–33, Medline.
Kaghad et al., 1994, *Gene*, 140:273–278.
Misra, 1974, *The Journal of Biological Chemistry*, pp. 2151–2155.
Nonogaki et al., 1991, *Human Reproduction*, 6(9):1305–1310.
Ohira et al., 1994, *Laboratory Investigation*, 70(2):279–285.
Rosenfeld et al., 1984, *J. Pediatr.* 105:781–785.
Toledano et al., 1991, *Proc. Natl. Acad. Sci. USA*, 88:4328–4332.
Wakasugi et al., 1990, *Proc. Natl. Acad. Sci. USA*, 87:8282–8286.
White et al., 1995, *Oxgen '95*, 2nd Annual Meeting of the Oxygen Society, Abstract Form.
Yagi et al., 1994, *J. Thorac. Cardiovasc Surg.*, 108:913–21.
Yamauchi et al., 1992, *Molecular Immunology*, 29(2):263–270.

*Primary Examiner*—Cecilia J. Tsang
*Assistant Examiner*—Abdel A. Mohamed
*Attorney, Agent, or Firm*—Sheridan Ross P.C.

[57] ABSTRACT

A method to increase cellular MnSOD production in an animal to treat oxidative damage by administering a protein having a thioredoxin active-site in reduced state. A composition and a method to protect an animal from lung disease are provided.

37 Claims, 11 Drawing Sheets

USE OF THIOREDOXIN-LIKE MOLECULES FOR INDUCTION OF MNSOD TO TREAT OXIDATIVE DAMAGE

CROSS REFERENCE TO RELATED APPLICATION

The present application claims priority from U.S. Provisional Application Ser. No. 60/020,740, filed Jun. 28, 1996.

GOVERNMENT RIGHTS

This invention was made in part with government support under HL 46481 and 1RO1 HL 52732, both awarded by the National Institutes of Health. The government has certain rights to this invention.

FIELD OF THE INVENTION

The present invention generally relates to a method to treat oxidative damage in an animal, in particular, by increasing the cellular level of MnSOD in an animal.

SUMMARY OF THE INVENTION

One embodiment of the present invention is directed to a method to increase the cellular level of MnSOd in an animal to treat oxidative damage. Such a method comprises administering to an animal an amount of a protein containing a thioredoxin active-site in reduced state which is effective to induce the production of MnSOD in an animal. In a preferred embodiment, a protein of the present invention is administered to an animal by a route selected from the group of nasal, inhaled and intratracheal routes. In another embodiment, such a protein has a preferred half-life in an animal of between about 16 and about 24 hours. In yet another embodiment, a protein containing a thioredoxin active-site in reduced state comprises the amino acid sequence C-G-P-C.

Another embodiment of the present invention relates to a composition for increasing the cellular level of MnSOD in an animal to treat oxidative damage. Such a composition comprises a protein containing a thioredoxin active-site in reduced state. Such a protein is formulated in a pharmaceutically acceptable delivery vehicle which provides a half-life of between about 5 minutes and about 24 hours in an animal.

Yet another embodiment of the present invention is a method to protect an animal from a lung disease by increasing the cellular level of MnSOD in the animal. Such method comprises administering to an animal a protein comprising the amino acid sequence X-C-X-X-C-X, wherein the C amino acid residues are in reduced state. Such a protein is effective to induce the production of MnSOD in an animal.

BACKGROUND OF THE INVENTION

Oxidative damage to cells can occur in various lung diseases, cancer and inflammatory diseases, and in other conditions involving hypoxia or ischemia-reperfusion injury, such as organ transplantation. Such damage is caused by the accumulation of oxygen-free radicals and active oxidation species in cells, or by direct oxygen toxicity.

Antioxidants, such as superoxide dismutase (SOD), catalase (CAT), components of the glutathione redox system, antiproteases, and Vitamin E, can react with and neutralize free radicals and oxidation species, and are thus a key defense mechanism against oxidative damage in a cell. Therefore, such antioxidants (or other elements involved in the production of such antioxidants) are excellent targets for methods of treating or preventing oxidative damage.

An important endogenous cellular antioxidant is manganese superoxide dismutase (MnSOD). MnSOD is a mitochondrial enzyme which dismutates potentially toxic superoxide radical into hydrogen peroxide and dioxygen. This enzyme is critical for protection against cellular injury due to elevated partial pressures of oxygen. MnSOD can be induced by sublethal hyperoxia, hydrogen peroxide and cytokines such as TNF-α or IL-1. Hence, it has been proposed that MnSOD is regulated through a mechanism involving an oxidative stress response (i.e. is activated by oxidants). MnSOD reequilibrates cellular redox balance by diminishing oxidative stress.

Prior investigators have used various methods to attempt to treat and/or prevent oxidative damage. For instance, exogenously produced antioxidants, such as recombinant MnSOD or CAT, have been delivered directly to animals in which oxidative damage was induced. Delivery of exogenous antioxidants has met with limited success, however, and it is not clear that such treatment is effective clinically. Such methods have failed to deliver the antioxidant into the cell and, in the case of MnSOD, specifically to the mitochondrion where it is needed. Moreover, delivery of low molecular weight "mimetopes" of such compounds paradoxically increases toxicity when a cell's oxygen tension is increased.

Furthermore, at the time of the present invention, all described means of inducing endogenous production of an antioxidant, such as MnSOD, have involved administration of toxic substances such as bacterial endotoxin, bacterial toxic component lipid A, tumor necrosis factor (TNF), or interleukin-1 (IL-1). These inflammatory reagents can contribute to septic shock syndrome and adult respiratory distress syndrome (ARDS). Thus, there remains a need for methods by which antioxidants such as MnSOD can be safely and effectively administered or induced.

Despite research efforts directed toward the elucidation of cellular pathways involved in protection against oxidative damage, the mechanisms by which such pathways are induced and operate have not been clearly defined. Thus, there remains a need to identify effective clinical methods by which oxidative damage can be prevented or treated.

DETAILED DESCRIPTION OF THE INVENTION

Figure 1:
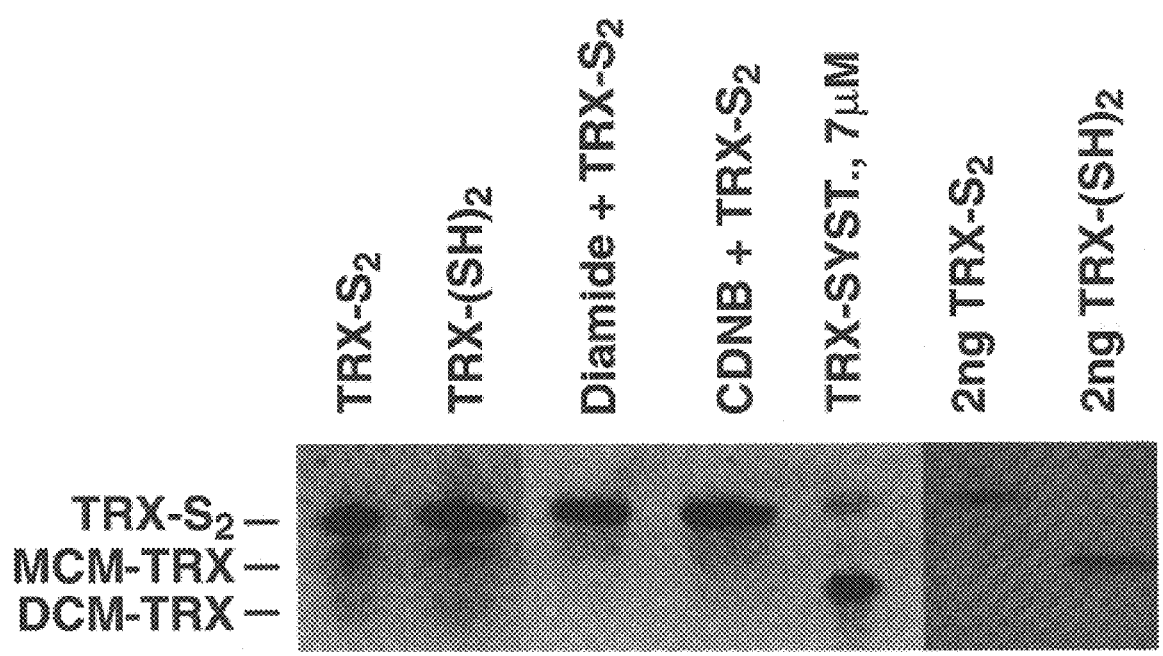
FIG. 1 is a Western blot showing the redox state of *E. coli* thioredoxin that has been externally added to human lung adenocarcinoma cells.

The present invention relates to a method and composition for increasing the cellular level of MnSOD in an animal to treat oxidative damage. Such a method comprises administering to an animal an amount of a protein containing a thioredoxin active-site in reduced state, such protein being effective to induce production of MnSOD.

Prior to the present invention, as previously discussed herein, it was thought that MnSOD production was induced by an oxidative stress response such as that induced by sublethal hyperoxia, hydrogen peroxide or cytokines such as TNF-α or IL-1. Therefore, it was thought that the mechanism of MnSOD production was through activation by oxidants. In addition, prior to the present invention, it was thought that thioredoxin was involved in protection against oxidative damage by directly scavenging reactive oxygen species. The present inventors have identified the paradoxical induction of manganese superoxide dismutase by the endogenous reductant thioredoxin and have elucidated a novel signal transduction role for this protein.

Thioredoxin (TXR) is a potent protein disulfide reductase found in most organisms which participates in many thiol-dependent cellular reductive processes. In addition to its ability to effect the reduction of cellular proteins, it is recognized that thioredoxin can act directly as an antioxidant (e.g. by preventing oxidation of an oxidizable substrate by scavenging reactive oxygen species) or can increase the oxidative stress in a cell by autoxidizing (e.g. generating superoxide radicals through autoxidation). As discussed above, prior to the present invention, it was not appreciated that thioredoxin could directly induce the production of MnSOD, nor that such induction would be effected by thioredoxin in reduced state. Thus, the present novel finding that reduced thioredoxin, a reductant, can induce MnSOD is an unexpected and surprising observation.

The present inventors have shown for the first time that MnSOD gene upregulation can be caused by conditions other than those of oxidative stress. Such a discovery leads to the disclosure herein of the novel method to treat oxidative damage in an animal by administration of a protein having a thioredoxin active-site in reduced state that is effective to induce production of cellular MnSOD. In addition to being surprising and unexpected, induction of MnSOD production by reductant thioredoxin is advantageous over other previously disclosed methods to treat oxidative damage. Since the method of the present invention does not require an oxidative environment to be effective, the protein of the present invention can be administered without the addition of potentially toxic inflammatory compounds, and is therefore safe to use and is effective for the prevention as well as the treatment of oxidative damage. For protein substrates, a very low concentration of reduced thioredoxin is required to effect induction of MnSOD. Therefore, a protein containing a thioredoxin active-site is effective to induce MnSOD production in very small doses and can be administered in safe, yet effective amounts.

Prior investigators have reported the use of thioredoxin to treat various conditions. For instance, U.S. Pat. No. 4,771,036 teaches that "thioredoxin compounds" can be topically applied to the eye to reduce disulfide bonds of oxidized lens proteins involved in cataract formation, thus preventing or reducing a cataractous condition (Pigiet et al., U.S. Pat. No. 4,771,036). Pigiet et al., however, only teach the use of thioredoxin to directly reduce cataract proteins, and do not teach the novel use of a protein containing a thioredoxin active-site that is effective to induce production of MnSOD. Other investigators have reported the intravenous injection of thioredoxin to treat post-ischemia tissue injury in rats or dogs (Fukuse, et al., pp. 387–391, 1995, *Thorax*, Vol. 50; Yagi et al., pp. 913–921, 1994, *J. Thorac. Cardiovasc. Surg.*, Vol. 108). These studies measured only the physiological effects of thioredoxin on ischemia and suggested that thioredoxin was acting as an antioxidant (scavenger of free radicals). Furthermore, thioredoxin was administered intravenously in these studies, and was therefore only present for a very short time at the site of damage, if at all. In these studies, it is unlikely that thioredoxin would have been present for a sufficient time to induce the production of MnSOD protein, nor was there any demonstration that thioredoxin even went to the specific site of damage, the lung. Such reports do not disclose or suggest a method or composition of the present invention to administer a protein having a thioredoxin active-site in reduced state such that the protein is effective to increase the cellular level of MnSOD in an animal to treat oxidative damage.

One embodiment of the present invention relates to a protein containing a thioredoxin active-site in reduced state effective to induce production of MnSOD. As described previously, thioredoxin is a protein disulfide reductase found in most organisms which participates in many thiol-dependent cellular reductive processes. In humans, thioredoxin is also referred to as adult T cell leukemia-derived factor (ADF). Intracellularly, most of this ubiquitous low molecular weight (11,700) protein remains reduced. Reduced or oxidized thioredoxin can enter intact cells. It has two vicinal cysteine residues at the active-site which in the oxidized protein form a disulfide bridge located in a protrusion from the protein's three dimensional structure. The flavoprotein thioredoxin reductase catalyzes the NADPH-dependent reduction of this disulfide. Small increases in thioredoxin can cause profound changes in sulfhydryl-disulfide redox status in proteins.

Remarkably low concentrations of thioredoxin are effective in reducing disulfides in insulin, fibrinogen, human chorionic gonadotropin, blood coagulation factors, nitric oxide synthase, ribonucleotide reductase, glucocorticoid receptors and other proteins. The rate of reduction of insulin disulfide by thioredoxin has been found to be 10,000 times higher than that by DTT. Thus, reduced thioredoxin is an extremely potent protein disulfide reductase.

A "thioredoxin active-site" of the present invention comprises the amino acid sequence C-X-X-C, disclosed in SEQ ID NO:1. As used herein, amino acid residues denoted "C" are cysteine residues and amino acid residues denoted "X"

can be any amino acid residue, and in particular, any of the standard 20 amino acid residues. Such a thioredoxin active-site of the present invention preferably comprises the amino acid sequence C-G-P-C, disclosed in SEQ ID NO:2. A thioredoxin active-site can further comprise the amino acid sequence X-C-X-X-C-X, disclosed in SEQ ID NO:3. Preferably, a thioredoxin active-site of the present invention comprises the amino acid sequence X-C-G-P-C-X, disclosed in SEQ ID NO:4, wherein such amino acid residue denoted "G" is a glycine residue, and wherein such amino acid residue denoted "P" is a proline residue. More preferably, a thioredoxin active-site of the present invention comprises the amino acid sequence W-C-G-P-C-K, disclosed in SEQ ID NO:5, wherein such amino acid residue denoted "W" is a tryptophan residue, and wherein such amino acid residue denoted "K" is a lysine residue. The phrase "in reduced state" specifically describes the state of the cysteine residues in the active-site of a protein of the present invention. In reduced state, such cysteine residues form a dithiol (i.e. two free sulfhydryl groups, —SH). In contrast, in oxidized form, such cysteine residues form an intramolecular disulfide bridge; such a molecule can be referred to as cystine. In reduced state, a thioredoxin active-site is capable of participating in redox reactions through the reversible oxidation of its active-site dithiol, to a disulfide, and catalyzes dithiol-disulfide exchange reactions.

It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", "containing" and "having" can be used interchangeably.

As used herein, a protein of the present invention containing a thioredoxin active site can be a thioredoxin active site per se or a thioredoxin active site joined to other amino acids by glycosidic linkages. Thus, the minimal size of a protein of the present invention is from about 4 to about 6 amino acids in length, with preferred sizes depending on whether full-length, fusion, multivalent, or merely functional portions of such a protein is desired. Preferably, the length of a peptide of the present invention extends from about 4 to about 40 amino acid residues. In a further preferred embodiment, a protein of the present invention can be a full-length protein or any homologue of such a protein, such as a protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitation, amidation and/or addition of glycosylphosphatidyl inositol) such that the homologue has a thioredoxin active-site that, in reduced state, is capable of inducing MnSOD production. As used herein, a protein containing a thioredoxin active-site can have characteristics similar to thioredoxin, and preferably, is thioredoxin selected from the group of prokaryotic thioredoxin, yeast thioredoxin, or mammalian thioredoxin. Preferably, a prokaryotic thioredoxin is E. coli thioredoxin. More preferably, a thioredoxin protein of the present invention is human thioredoxin.

A protein of the present invention can also be a fusion protein that includes a segment containing a thioredoxin active-site and a fusion segment that can have a variety of function. For example, such a fusion segment can function as a tool to simplify purification of a protein of the present invention, such as to enable purification of the resultant fusion protein using affinity chromatography. A suitable fusion segment can be a domain of any size that has the desired function (e.g., imparts increased stability to a protein, imparts increased immunogenicity to a protein, and/or simplifies purification of a protein). It is within the scope of the present invention to use one or more fusion segments. Fusion segments can be joined to amino and/or carboxyl termini of the segment containing a thioredoxin active-site. Linkages between fusion segments and thioredoxin active-site-containing domains of fusion proteins can be susceptible to cleavage in order to enable straight-forward recovery of the thioredoxin active-site-containing domains of such proteins. Fusion proteins are preferably produced by culturing a recombinant cell transformed with a fusion nucleic acid molecule that encodes a protein including the fusion segment attached to either the carboxyl and/or amino terminal end of an thioredoxin active-site-containing domain.

In one embodiment, a protein containing a thioredoxin active-site suitable for use with the method of the present invention comprises a protein containing a thioredoxin active-site derived from a substantially similar species of animal to which the protein is to be administered. For example, if the protein is to be administered to a human patient, then preferably primate, and more preferably human protein containing a thioredoxin active-site can be used to treat or protect the animal from a condition involving oxidative damage. If the protein containing a thioredoxin active-site is to be administered to a mouse, then preferably rodent (i.e., hamster, rat, guinea pig), and more preferably mouse protein can be used. A preferred protein containing a thioredoxin active-site of the present invention includes such a protein derived from prokaryotes, yeast and mammals. More preferred protein containing a thioredoxin active-site includes protein containing a thioredoxin active-site derived from humans.

In another embodiment, a protein containing a thioredoxin active-site suitable for use with the method of the present invention comprises an isolated, or biologically pure, protein which has been removed from its natural milieu. As such, "isolated" and "biologically pure" do not necessarily reflect the extent to which the protein has been purified. An isolated protein of the present invention can, for example, be obtained from its natural source, be produced using recombinant DNA technology (e.g., polymerase chain reaction (PCR) amplification, cloning), or be synthesized chemically. Preferably, a protein containing a thioredoxin active-site of the present invention includes recombinantly produced protein containing a thioredoxin active-site.

A protein of the present invention can be produced recombinantly by transforming a host cell with one or more nucleic acid molecules encoding such protein. Such nucleic acid molecules are typically operatively linked to an expression vector containing one or more transcription control sequences. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. Transformed nucleic acid molecules can remain extrachromosomal or can integrate into one or more sites within a chromosome of the transformed (i.e., recombinant) cell in such a manner that their ability to be expressed is retained.

In accordance with the present invention, such recombinant cells can be used to produce one or more proteins or peptides of the present invention by culturing such cells under conditions effective to produce such a protein, and recovering the protein. Effective conditions to produce a protein include, but are not limited to, appropriate media, bioreactor, temperature, pH and oxygen conditions that permit protein production. The recombinant proteins can be recovered and purified using a variety of standard protein purification techniques known in the art.

As described previously herein, MnSOD, or manganese superoxide dismutase, is a mitochondrial enzyme which dismutates superoxide radicals in most mammalian cell types. MnSOD protects critical targets of superoxide in addition to preventing subsequent formation of its potentially more toxic free radical by-products.

According to the present invention, a "cellular level of MnSOD" is a level, a concentration, or amount, of MnSOD that is produced by a cell in an animal. Such production of MnSOD can be the natural, or endogenous, production of MnSOD that occurs in the normal cycle and environment of a cell. Such production of MnSOD can also be production of MnSOD that occurs as a result of manipulation or modulation of such MnSOD production in a cell by the application of the present invention. As used herein, an increase in the cellular level of MnSOD comprises an increase, augmentation or expansion in the level of MnSOD gene expression by a cell (i.e. transcription of MnSOD mRNA) or an increase, augmentation or expansion in the level of MnSOD protein expression by a cell. Such an increase can be relative to a basal, resting, or uninduced cellular level of MnSOD in cells of the same type, or relative to the cellular level of MnSOD prior to administration of a protein containing a thioredoxin active-site of the present invention. An increase in the cellular level of MnSOD can be detected by any standard means known in the art (e.g. detection of increased MnSOD mRNA production by PCR or Northern blot or detection of increased MnSOD protein or enzyme activity by Western blot or enzyme assay).

As previously disclosed herein, a novel aspect of the present invention is a thioredoxin active-site in reduced state that is effective to induce the production of MnSOD. The term "MnSOD production", as used herein, refers to the production of a detectable amount of MnSOD gene expression or MnSOD protein expression by a cell. To induce MnSOD production can be to initiate, to increase, to upregulate, to augment or to expand the production, or expression, of MnSOD mRNA and/or MnSOD protein. Without intending to be bound by theory, such induction of MnSOD production comprises a direct reductant mechanism of action of a thioredoxin active-site on MnSOD production. Such mechanism is not effected by such thioredoxin active-site directly functioning as an antioxidant, or by such thioredoxin active-site autooxidizing.

Thioredoxin which directly functions as an antioxidant delays or prevents oxidation of an oxidizable substrate by scavenging or reacting with the reactive oxygen species which otherwise would oxidize such substrate. Such antioxidant function occurs in an oxidative environment. Thioredoxin can also autooxidize, which increases the oxidative stress in the environment. Such oxidative stress can then result in induction of cellular protective mechanisms. The present inventors demonstrate herein that thioredoxin or a protein containing thioredoxin active-site effects the induction of MnSOD by a reductant pathway. Such a reductant pathway is effected by said thioredoxin active-site being in reduced state. Without being bound by theory, the present inventors believe that a reductant thioredoxin active-site activates a signal transducing protein, nuclear transcription factor κB (NFκB), a transcription factor which induces MnSOD gene expression. This effect occurs through a complex and specific molecular interaction, in which an oxidized form of NFκB apparently must be reduced to exert its DNA binding activity. Oxidized thioredoxin is unable to activate NFκB. Therefore, thioredoxin functioning through autoxidation or antioxidant activity can not activate NFκB. Moreover, activation of NFκB by thioredoxin specifically activates MnSOD production. Since thioredoxin in oxidized state is not effective to induce MnSOD production, previously disclosed oxidant mechanisms for thioredoxin function are not encompassed in the methods the present invention.

Oxidative damage refers to cellular damage that occurs as a result of the accumulation of oxygen-free radicals and other oxidative species in cells. Such oxygen-free radicals and oxidative species (e.g. hydrogen peroxide) result from reactive oxygen intermediates produced during various types of stress, caused by conditions such as lung disease, ischemia, hypoxia, exposure to ozone, hyperoxia, inflammatory responses, chemical reactions, ultraviolet or X-ray irradiation, or viral infection. In one embodiment, a method to increase the cellular level of MnSOD in an animal to treat oxidative damage in such an animal is particularly useful when such animal has a condition selected from the group of lung disease, cancer, hypoxia, ischemia reperfusion injury, atherosclerosis, and inflammatory disease. "A condition", as used herein, refers to a disease, or any deviation from normal health of an animal and includes disease symptoms as well as conditions in which a deviation (e.g., infection, environmental trigger, gene mutation, genetic defect, etc.) has occurred but symptoms are not yet manifested. Having a condition, therefore, can include being predisposed to such a condition or disease (e.g. due to genetic predisposition or predisposition due to environmental factors or other medical conditions or procedures).

Hypoxia is a condition characterized by abnormally low levels of oxygen in the blood and tissues. Ischemia-reperfusion injury is a type of injury that is due to damage to a tissue resulting from oxygenation deficiency caused by restriction of blood supply to the tissue. Ischemia reperfusion injury often occurs after organ transplantation. Examples of lung diseases for which a method of the present invention can be particularly useful to treat include, but are not limited to, infant respiratory distress syndrome, adult respiratory distress syndrome, interstitial lung disease, and asthma. The method of the present invention is also useful to treat various inflammatory diseases including, but not limited to, rheumatoid arthritis, inflammatory bowel disease, and several inflammatory skin diseases.

As used herein, the phrase "to treat oxidative damage in an animal" refers to reducing the level of oxidative damage in an animal wherein such damage has already occurred, is occurring, will occur in the future, or may occur in the future. In one embodiment of the present invention, "to treat" oxidative damage can also mean "to protect" an animal from oxidative damage. Preferably, oxidative damage, or the potential for oxidative damage, is reduced, optimally, to an extent that the animal no longer suffers discomfort and/or altered function from oxidative damage. For example, treating an animal can refer to the ability of a compound, when administered to the animal, to prevent oxidative damage from occurring and/or cure or alleviate disease symptoms, signs or causes. When used to protect an animal from oxidative damage, such treatment can therefore be administered prior to the potential for such damage to occur. In particular, treating an animal refers to modulating oxidative damage to suppress (e.g., reduce, inhibit or block) such damage.

According to the present invention, an amount of a protein containing a thioredoxin active-site is administered to an animal to treat oxidative damage. Such protein is effective to induce cellular MnSOD production in such animal. An animal for which a method and/or composition of the present invention is useful is preferably a mammal, and more preferably, a human.

A suitable, or effective, amount of a protein containing a thioredoxin active-site to administer to an animal is an amount that is capable of treating oxidative damage in an animal by induction of MnSOD, or protecting an animal from a lung disease by inducing the production of MnSOD in an animal. For example, a suitable amount of such a protein is capable of treating oxidative damage in an animal when administered one or more times over a suitable time period. In particular, a suitable amount of a protein containing a thioredoxin active-site comprises an amount that increases the cellular level of MnSOD in the animal at least about 2-fold. Preferably, the cellular level of MnSOD is increased at least about 5-fold, and more preferably at least about 10-fold, and even more preferably, at least about 15-fold.

A preferred amount of a protein containing a thioredoxin active-site to be administered to an animal comprises between about 1.5 micromoles×kilogram$^{-1}$ and about 150 micromoles×kilogram$^{-1}$ body weight of an animal. A more preferred amount of a protein containing a thioredoxin active-site to be administered to an animal comprises between about 2 micromoles×kilogram$^{-1}$ and about 25 micromoles×kilogram$^{-1}$ body weight of an animal. An even more preferred amount of a protein containing a thioredoxin active-site to be administered to an animal comprises between about 3 micromoles×kilogram$^{-1}$ and about 10 micromoles×kilogram$^{-1}$ body weight of an animal. The optimum amount of a protein of the present invention to be administered to an animal will vary depending on the route of administration. For instance, if the protein is administered by an inhaled route, the optimum amount to be administered may be different than the optimum amount to be administered by intratracheal injection. It is within the ability of one skilled in the art to vary the amount depending on such route of administration. It is important to note that a suitable amount of a protein of the present invention is an amount that has the desired function without being toxic to an animal.

In accordance with the present invention, acceptable protocols to administer a protein containing a thioredoxin active-site include the mode of administration and the effective amount of a protein containing a thioredoxin active-site administered to an animal, including individual dose size, number of doses and frequency of dose administration. Determination of such protocols can be accomplished by those skilled in the art. Suitable modes of administration can include, but are not limited to, oral, nasal, intratracheal injection, inhaled, transdermal, rectal, and parenteral routes. Preferred parenteral routes can include, but are not limited to, subcutaneous, intradermal, intravenous, intramuscular and intraperitoneal routes. In a preferred embodiment of the present invention, a protein containing a thioredoxin active-site is administered by inhalation (i.e. by inhaling an aerosol) or intratracheally (i.e. by injection directly into the trachea), either directly or via lipid-encapsulation or surfactant. A protein containing a thioredoxin active-site of the present invention is not administered by topical surface administration to the skin or other surface of an animal.

In a preferred embodiment, a protein of the present invention has a half-life in an a animal that is sufficient to induce MnSOD at an effective rate and amount to treat oxidative damage in the animal. Such half-life can be effected by the method of delivery of such a protein. A protein of the present invention preferably has a half-life of greater than about 5 minutes in an animal, and more preferably greater than about 4 hours in an animal, and even more preferably greater than about 16 hours in an animal. In a preferred embodiment, a protein of the present invention has a half-life of between about 5 minutes and about 24 hours in an animal, and preferably between about 2 hours and about 16 hours in an animal, and more preferably between about 4 hours and about 12 hours in an animal.

Preferably, a protein containing a thioredoxin active-site of the present invention is administered in a pharmaceutically acceptable delivery vehicle. In a more preferred embodiment, such a delivery vehicle is capable of slowly releasing the protein containing a thioredoxin active-site or the composition of the present invention into an animal. Pharmaceutically acceptable delivery vehicles include, but are not limited to, liposomes, recombinant cells, biocompatible polymers, other polymeric matrices, capsules, microcapsules, microparticles, bolus preparations, osmotic pumps, diffusion devices, liposphere, transdermal delivery systems, and surfactants. Other delivery vehicles of the present invention include liquids that, upon administration to an animal, form a solid or a gel in situ. Particularly preferred delivery vehicles of the present invention include lipid capsules or surfactants. Preferred delivery vehicles are also biodegradable (i.e., bioerodible).

A preferred delivery vehicle of the present invention is capable of maintaining a protein containing a thioredoxin active-site of the present invention in the blood of an animal or preferably at the site undergoing oxidative damage such that the half-life of the protein in the animal is sufficient to induce MnSOD at an effective rate and amount to treat said oxidative damage. A protein containing a thioredoxin active-site of the present invention that is administered in the context of a pharmaceutically acceptable delivery vehicle of the present invention preferably has a half-life in an animal that is greater than about 5 minutes in an animal, and more preferably greater than about 4 hours in an animal, and even more preferably greater than about 16 hours in an animal. In a preferred embodiment, a protein containing a thioredoxin active-site of the present invention that is administered in the context of a pharmaceutically acceptable delivery vehicle of the present invention has a half-life of between about 5 minutes and about 24 hours in an animal, and preferably between about 2 hours and about 16 hours in an animal, and more preferably between about 4 hours and about 12 hours in an animal.

Another embodiment of the present invention relates to a composition for increasing the cellular level of MnSOD in an animal to treat oxidative damage. Such composition comprises a protein containing a thioredoxin active-site in reduced state formulated with a pharmaceutically acceptable delivery vehicle which provides a half-life of between about 5 minutes and about 24 hours in said animal. Pharmaceutically acceptable delivery vehicles of the present invention are previously described herein. Preferably, a composition of the present invention is formulated with a delivery vehicle selected from the group of liposomes, recombinant cells, biocompatible polymers, other polymeric matrices, capsules, microcapsules, microparticles, bolus preparations, osmotic pumps, diffusion devices, lipospheres, transdermal delivery systems, and surfactants. Most preferably, a composition of the present invention is formulated with a delivery vehicle selected from the group of liposomes, lipospheres and surfactants.

In another embodiment, a composition of the present invention comprising a protein containing a thioredoxin active-site can be administered simultaneously or sequentially with an effective amount of a compound capable of enhancing the ability of the protein to treat oxidative damage in an animal. For example, compositions of the present invention can be formulated with other compounds that the animal to be treated can tolerate. Examples of such compounds include water, saline, phosphate buffered solutions, Ringer's solution, dextrose solution, Hank's solution, polyethylene glycol-containing physiologically balanced salt solutions, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Such compounds can also contain minor amounts of additives, such as substances that enhance isotonicity and chemical stability or buffers. Examples of buffers include phosphate buffer, bicarbonate buffer and Tris buffer, while examples of preservatives include thimerosal, m- or o-cresol, formalin and benzyl alcohol. The choice of such a compound to be administered in conjunction with a protein of the present invention can be made by one of skill in the art based on various characteristics of the animal. In particular, such characteristics include an animal's genetic background, history of occurrence of condition leading to oxidative damage, and general physical well being.

In a preferred embodiment, a composition of the present invention is further formulated with thioredoxin reductase and/or NADPH. Preferably, a composition of the present invention is formulated with between about 10 mM and about 10 mM achieved surface concentration of NADPH, and more preferably, about 1 mM achieved surface concentration of NADPH. An "achieved surface concentration" is the concentration of a particular chemical, such as NADPH, that is achieved, or present, at the surface of a cell or tissue, for example, at the surface of lung epithelial lining. Therefore, it may be necessary to actually administer a larger concentration of a particular chemical in order to achieve a certain surface concentration. It is well within the ability of one skilled in the art to determine such concentrations. A composition of the present invention is preferably formulated with between about 0.01 units per liter and about 10 units per liter achieved surface concentration of thioredoxin reductase, and more preferably, about 0.1 unit/liter achieved surface concentration of thioredoxin reductase. It is within the scope of the present invention that such amounts of thioredoxin reductase and/or NADPH can be modified by one skilled in the art in order to maintain or enhance the reduced state of a thioredoxin active-site, as the amount of a protein containing such active-site or the mode of delivery indicates.

The following examples are provided for the purposes of illustration and are not intended to limit the scope of the present invention.

EXAMPLES

Example 1

The following example examines the redox status of externally added *E. coli* thioredoxin in A549 cells.

Human microvascular endothelial cells were obtained from Clonetics (San Diego, Calif.). Anti-*E. coli* thioredoxin and *E. coli* thioredoxin reductase were obtained from American Diagnostics (Greenwich, Conn.). Anti-human MnSOD was obtained from Calbiochem (San Diego, Calif.). Recombinant *E. coli* thioredoxin was obtained from Promega (Madison, Wis.). Iodoacetic acid was obtained from Sigma Chemical. All other chemicals were of highest available grade.

The human lung adenocarcinoma line A549 was obtained from ATCC (Rockville, Md.) and maintained in endotoxin free F-12K medium (Dr. Kaigan's modified, GIBCO) containing 10% fetal calf serum and 100 units of penicillin/streptomycin. Fully confluent monolayers were treated with different concentrations of thioredoxin for various time intervals and then washed twice with Hank's Balanced Salt Solution. Human lung microvascular endothelial cells (HMVEC) were grown in endothelial basal medium along with nutrient supplements (Clonetics), L929 (mouse fibroblast) cells were grown in Dulbecco's Minimal Essential Medium, monkey kidney cells (OMK) cells were grown in RPMI 1640 medium, and L2 (rat epithelial cell) cells were grown in F-12K media. All media were supplemented with 10% fetal calf serum.

*E. coli* thioredoxin-$S_2$ was reduced with a 5-fold molar excess of dithiothreitol under argon at room temperature for 20 minutes in argon-equilibrated 10 mM Tris-HCl, pH 7.5 containing 1 mM EDTA. Following this reaction, 1 mL of carboxymethylation/cell lysis buffer (0.1 M Tris, pH 8.8, 12 mg/ml iodoacetic acid, 3 mM EDTA, 7 M guanidine hydrochloride and 0.5% Triton X-100, equilibrated with argon for 1 hour) was added. The solution was incubated at 37° C. in the dark for 45 minutes. After incubation, excess reagent was removed by a Sephadex-G25 spin column. In a control experiment, when 2 mM DTT in 10 mM Tris, pH 7.5, 1 mM EDTA was passed through a Sephadex G-25 spin column, there was no DTT detected in the eluate as measured by reduction of 5.5'-dithio-bis(2-nitrobenzoic acid) at 412 nm. Cell lysates for determination of oxidation state of thioredoxin were processed similarly after cell monolayers were washed with phosphate-buffered saline. Protein was determined using a Bradford assay (Biorad, Ref. 30).

Before examining the effects of oxidized and reduced thioredoxin in A549 cells, it was of interest to determine whether thioredoxin was in reduced state within A549 cells. Because *E. coli* thioredoxin is not as effective a substrate as mammalian thioredoxin for mammalian thioredoxin reductase, and because of the oxidizing environment of cell culture medium, it was considered possible that the effect of thioredoxin would be mediated by its oxidized species. Specifically, the $K_m$ for *E. coli* thioredoxin is 35 $\mu$M, approximately 14 fold higher than the $K_m$ for mammalian thioredoxin.

A549 lysates and standards of oxidized and reduced thioredoxin (TRX-$S_2$ and TRX-$(SH)_2$, respectively) were prepared and the free sulfhydryl groups were carboxymethylated. The sulfhydryl group of cysteine-32 in *E. coli* thioredoxin-$SH_2$ shows a low apparent pKa value of 6.7. Only this sulfhydryl group of native thioredoxin $SH_2$ is alkylated by iodoacetic acid. In reduced thioredoxin which has been denatured by guanidine hydrochloride, both sulfhydryl groups are reactive. Carboxymethylated oxidized and reduced thioredoxin can therefore be separated in a 15% native polyacrylamide gel.

To detect thioredoxin redox state by Western blot, carboxymethylated A549 cell lysates (10 μg each) and carboxymethylated oxidized and reduced thioredoxin standards were separated on 15% native polyacrylamide gels. The protein was transferred to nitrocellulose (Hybond-ECL, Amersham) using a miniprotein transblot apparatus (Biorad). The nitrocellulose was washed and incubated with anti-sheep IgG to *E. coli* thioredoxin (American Diagnostics). After washing, the blot was incubated with sheep IgG-horseradish peroxidase conjugate for 1 hour at room temperature. Binding of secondary antibody was detected using an ECL detection system (Amersham).

Statistical analysis was done by microcomputer with JMP statistical software. Means were compared by one-way analysis of variance followed by Tukey's test for multiple comparisons, and a p-value <0.05 was considered significant.

When A549 cells were incubated with oxidized thioredoxin (14 μM; 16 h), about 45% of the total amount of internalized thioredoxin was found to be in monothiol and dithiol form. Approximately 8% was found to be in dithiol form as it could form dicarboxymethylated thioredoxin, and about 37% was present in the monothiol form which could be detected as monocarboxymethylated thioredoxin. *E. coli* thioredoxin can be a substrate for human thioredoxin reductase, although the $K_m$ is about 35 μM. Therefore, it is likely that at higher concentrations of *E. coli* thioredoxin, partial reduction by the endogenous human thioredoxin reductase occurs, thus explaining the 8% of oxidized *E. coli* thioredoxin that was fully reduced, and the 37% that had been converted to a partially reduced form.

FIG. 1 shows three distinct bands in the alkylated homogenates of A549 cells incubated with oxidized or reduced thioredoxin (14 μM; FIG. 1, lanes 1 & 2). The bands were identified as follows: the uppermost band is the oxidized thioredoxin (TRX-S$_2$) as determined from the standard, and the bottom band is the dicarboxymethylated thioredoxin (DCM-TRX). This is the product of reduced thioredoxin in which both cysteines, cys-32 and cys-35, are in the reduced state and are carboxymethylated. The intermediate band corresponds to the monocarboxymethylation product of cys-32 (MCM-TRX). Cys-32 is the most reactive sulfhydryl in TRX-SH$_2$. Therefore, both of the lower bands are referred to as reduced thioredoxin (TRX-SH$_2$) for calculation of the total percentage in the reduced state. Thus, a relatively small amount of internalized *E. coli* thioredoxin (8%) was fully reduced by A549 cells.

Figure 2:
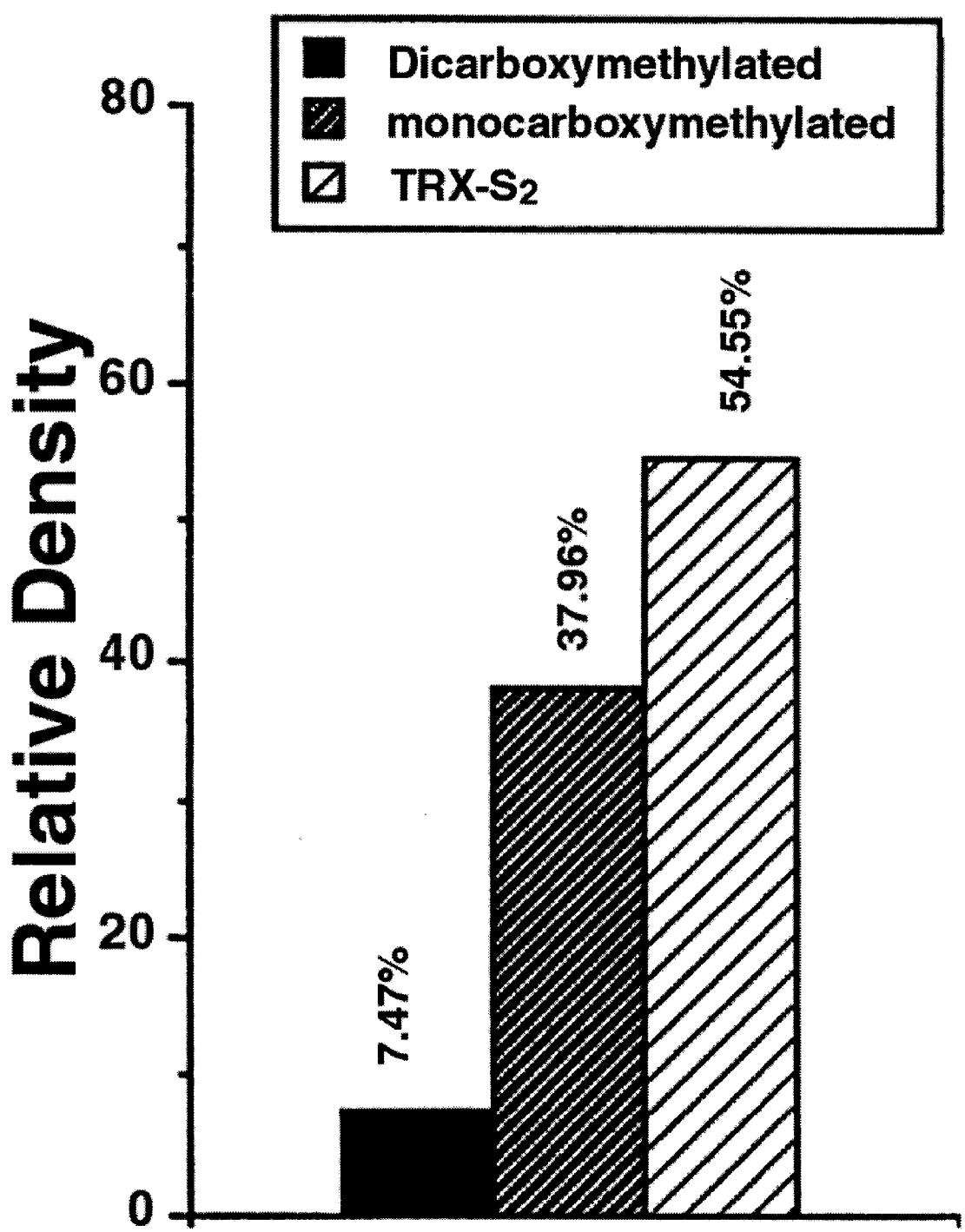
FIG. 2 shows the relative densities of different redox states of *E. coli* thioredoxin that has been externally added in oxidized state to human lung adenocarcinoma cells.
Figure 3:
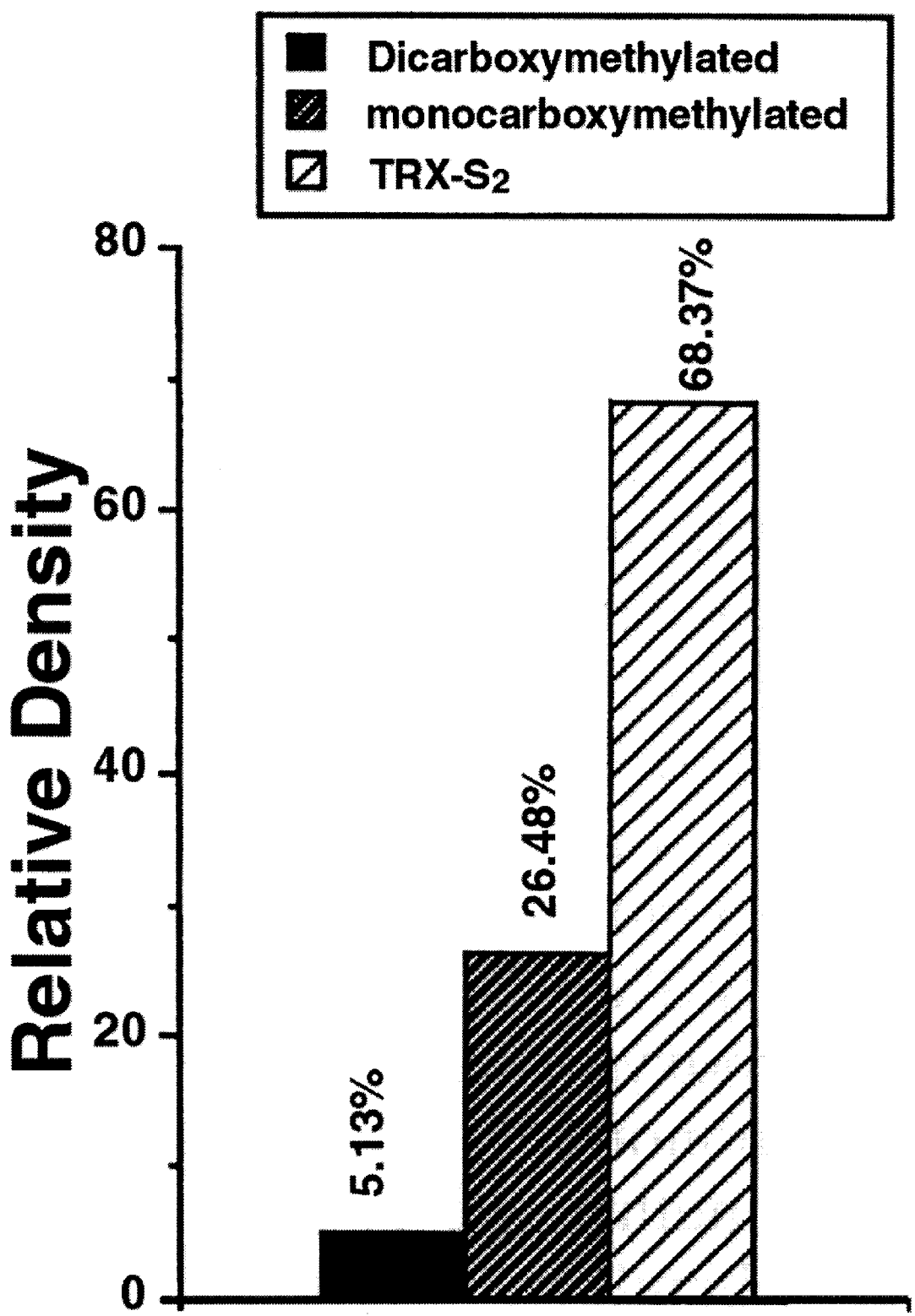
FIG. 3 shows the relative densities of different redox states of *E. coli* thioredoxin that has been externally added in reduced state to human lung adenocarcinoma cells.

Densitometry of lanes 1 and 2 of FIG. 1 were performed on an Apple Image Scanner and the results were plotted as relative densities (percentage of total) for each of the three bands (FIGS. 2 and 3). FIG. 2 shows that when A549 cells were incubated with 14 μM TRX-S$_2$, different redox states of thioredoxin were detected by carboxymethylation of cell lysates followed by Western blot analysis as follows: 7.47% DCM-TRX, 37.9% MCM-TRX, and 54.55% TRX-S$_2$ (DCM-TRX: dicarboxymethylated thioredoxin; MCM-TRX: monocarboxymethylated thioredoxin).

FIG. 3 shows that when A549 cells were incubated with 14 μM TRX-(SH)$_2$ reduced by DTT, these species were detected: 5.13% DCM-TRX, 26.49% MCM-TRX, and 68.37% TRX-S$_2$.

A549 cells were incubated with thioredoxin (7 μM) plus NADPH (2 mM) and *E. coli* thioredoxin reductase (0.1 μM), In the presence of this reducing system, 85% of the *E. coli* thioredoxin which entered A549 cells was fully reduced (FIG. 1, lane 5).

FIG. 1 shows the Western blot, with the lanes as follows: lane 1, lysates of A549 cells incubated with TRX-S$_2$ (14 μM; 16 h); lane 2, lysates of A549 cells incubated with DTT reduced TRX-(SH)$_2$ (14 μM; 16 h); lane 3, lysate of A549 cells incubated with diamide (2 mM; 30 min) followed by washing and addition of TRX-S$_2$ (14 μM; 6 h); lane 4, same as lane 3 but the cells were incubated with CDNB, a thiol alkylating agent (100 μM; 45 min) followed by addition of TRX-S$_2$ (14 μM); lane 5, lysate of A549 cells incubated with TRX-S$_2$ (7 μM), thioredoxin reductase (0.1 μM) and NADPH (2 mM) for 6 hours; lane 6, TRX-S$_2$ standard (2 ng); lane 7, carboxymethylated TRX-(SH)$_2$ (2 ng) standard.

Example 2

This example demonstrates the effect of different redox states of thioredoxin on induction of MnSOD mRNA.

Human MnSOD gene was obtained from ATCC in PHMNSOD4 plasmid in *E. Coli* HB101. Plasmids were amplified in *E. coli* and were purified with a QIAGEN plasmid preparation kit (QIAGEN Inc., Chatsworth, Calif.). The cDNAs were isolated from the vectors by treatment with EcoR1 and gel purified. cDNAs were labeled with randomly primed DNA labeling kit (GIBCO).

Reduced thioredoxin (recombinant, *E. coli*; Promega) was prepared by treating 1 mM thioredoxin with 2 mM dithiothreitol (DTT) for 20 min at room temperature followed by removal of excess DTT using a G-25 spin column. A549 cells were grown in F-12K medium with 10% serum. Confluent monolayers were treated with oxidized thioredoxin (3 or 7 μM), with and without the thioredoxin reducing system [thioredoxin reductase (0.1 μM)+NADPH (2 mM)]. Incubations were for 16 hours. Total RNA was isolated from cells by guanidine isothiocyanate lysis and cesium chloride centrifugation of the lysate (147,000× g, 20–25° C.) in an ultracentrifuge (Beckman) by the methods of Sambrook et al., ibid. Total RNA was quantified spectrophotometrically.

Twenty micrograms of RNA was resolved by electrophoresis in 1% agarose, 2.5 M formaldehyde gel in a buffer containing 20 mM MOPS and 1 mM EDTA (pH 7.4). RNA was transferred to nitrocellulose and blots were prehybridized 2–12 hours in 50% formamide, 0.75 M sodium chloride, 0.075 M sodium citrate (pH 7.0), 5× Denhardt's solution, 50 μg/ml salmon sperm DNA, and 0.1% SDS at 42° C. Blots were hybridized with cDNA for MnSOD labeled to a specific activity of 2–7×10$^7$ cpm using $^{32}$P-γ CTP (ICN) in hybridization solution at 42° C. overnight and then were washed in 0.3 M sodium chloride, 0.03 M sodium citrate, 0.1% SDS at 42° C. Autoradiographs were made by exposing blots to x-ray film (Kodak) at −70° C. with intensifying screens. Blots were exposed to phosphorimager screens (Molecular Dynamics) and densitometry was performed with a Macintosh computer using MD Image Quant Version 3.35.

Figure 4:
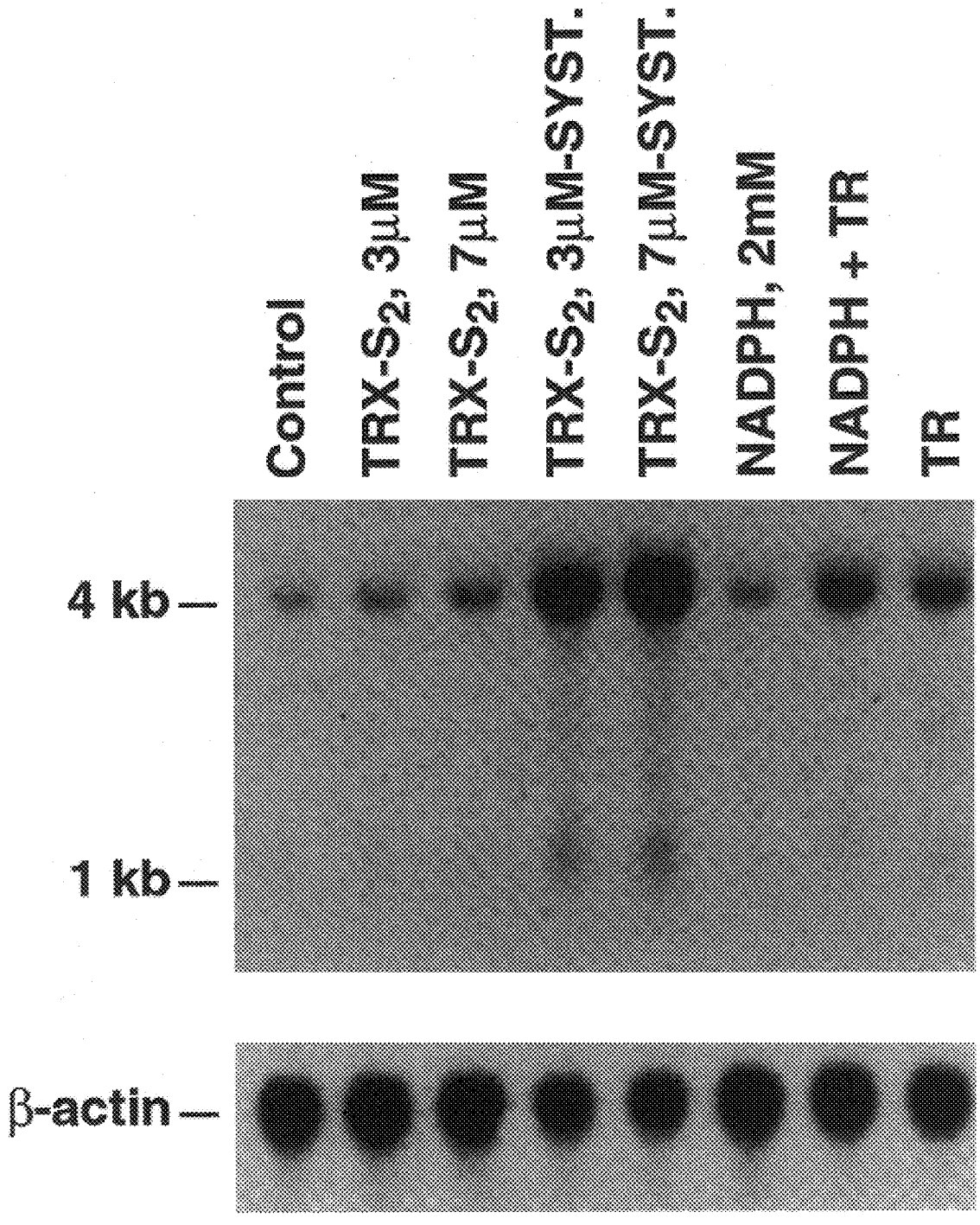
FIG. 4 is a Northern blot that illustrates the effects of various concent rations of oxidized or reduced thioredoxin on MnSOD mRNA production by human lung adenocarcinoma cells.

FIG. 4 shows the autoradiograph of the Northern blot. Lanes are as follows: lane 1, untreated control; lanes 2 and 3, oxidized thioredoxin (3 and 7 μM, respectively); lanes 4 and 5, oxidized thioredoxin (3 and 7 μM, respectively), thioredoxin reductase (0.1 μM), and NADPH (2 mM); lane 6, NADPH (2 mM); lane 7, thioredoxin reductase (0.1 μM) plus NADPH (2 mM); lane 8, thioredoxin reductase (0.1 μM). MnSOD mRNA (1 and 4 kb bands) is shown in the upper panel; B-actin mRNA is shown in the lower panel.

When A549 cells were incubated with high concentrations of oxidized or reduced thioredoxin (28 μM; 16 h), both induced expression of MnSOD mRNA with almost equal potency (data not shown). However, when these cells were incubated with lesser concentrations of oxidized thioredoxin (7 μM; 16 h), there was very little or no induction of MnSOD mRNA (FIG. 4). To determine whether the observed induction of MnSOD mRNA was due to reduced thioredoxin, the cells were incubated with oxidized thioredoxin (7 μM) along with the thioredoxin reducing system containing NADPH (2 mM) and thioredoxin reductase (0.1 μM). Under these reducing conditions, most of the E. coli oxidized thioredoxin enters the cell in the reduced state and remains reduced within the cells. Using these conditions, there was a 6-fold increase in MnSOD mRNA. Thus, an increase in MnSOD gene expression was detected when thioredoxin was found to be in the reduced state within treated A549 cells. On the contrary, little or no elevation of MnSOD gene expression was found when E. coli thioredoxin was present predominantly in an oxidized state. Hence, reduced thioredoxin causes increased MnSOD gene expression.

Since lower concentrations (3 or 7 μM) of oxidized thioredoxin only increased MnSOD expression when exposed to cells in the presence of a complete thioredoxin reducing system, it is clear that thioredoxin can induce MnSOD only in the reduced form. Likewise, it is apparent that the small amount of thioredoxin which was present in the reduced form when A549 cells were incubated with higher concentrations (28 μM) of oxidized thioredoxin (see Example 1), was responsible for MnSOD induction.

Example 3

The following example shows the effect of diamide and CDNB, a thiol alkylating agent, on MnSOD mRNA induction by thioredoxin.

Reduced thioredoxin is rapidly oxidized by diamide, whereas the thioredoxin reductase system can catalyze NADPH-dependent reduction of both diamide and thioredoxin. Thus, the oxidation of TRX-SH$_2$ by diamide is reversible.

To evaluate the effect of oxidation of TRX-SH$_2$ on MnSOD induction, A549 cells were incubated with diamide (2 mM; 30 min) or CDNB (100 μM; 45 min). After incubation, cells were washed and fresh medium added. The cells next were incubated with oxidized thioredoxin (28 μM; 6 h) and then processed for Northern analysis as described in Example 2.

Figure 5:
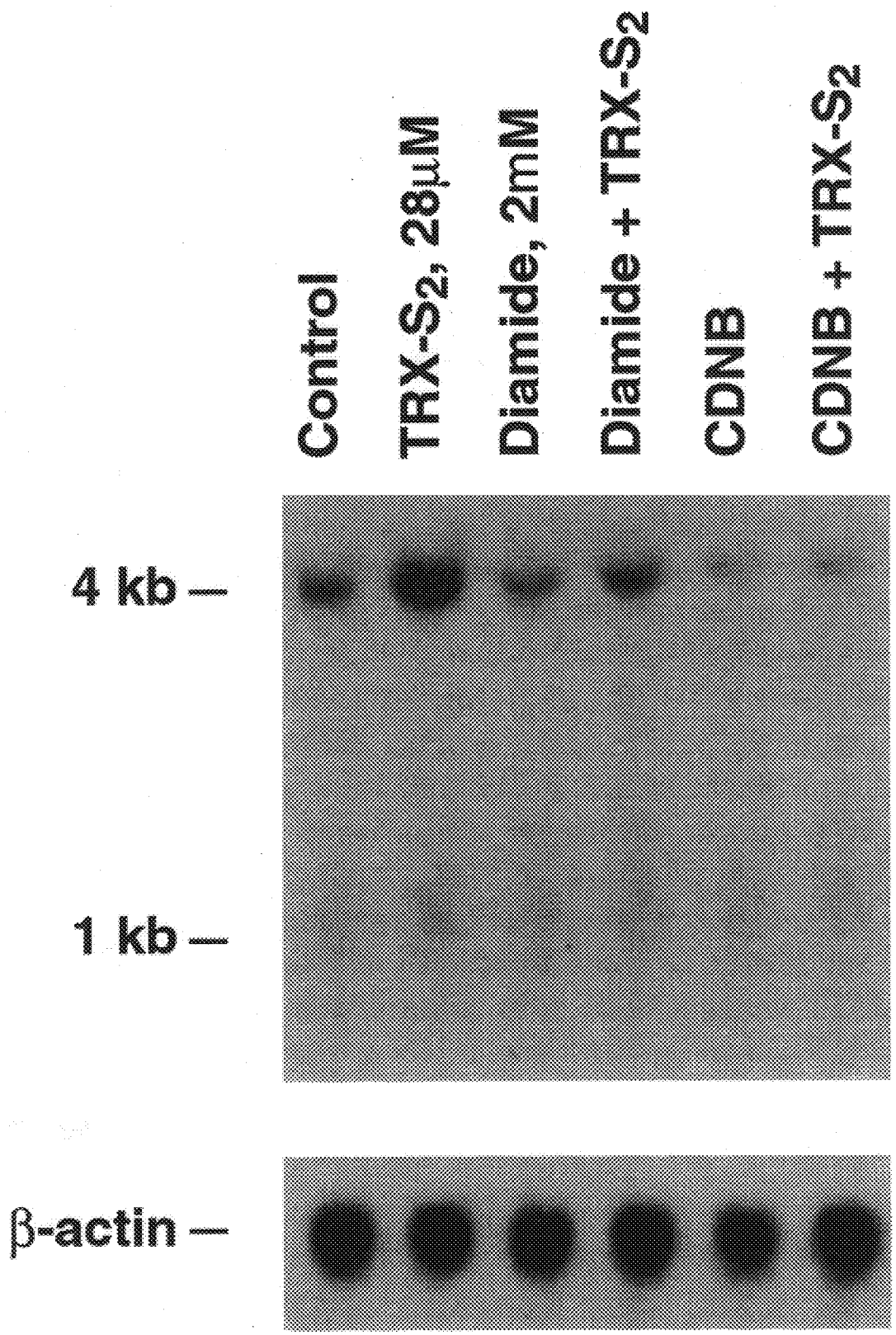
FIG. 5 is a Northern blot demonstrating the effect of the oxidizer, diamide, on MnSOD mRNA induction by reduced thioredoxin.

FIG. 5 shows the autoradiograph of the Northern blot, with the lanes loaded as follows: lane 1, untreated control; lane 2, TRX-S$_2$ (28 μM); lane 3, diamide (2 mM); lane 4, diamide (2 mM) plus TRX-S$_2$ (28 μM); lane 5, CDNB (100 μM); lane 6, CDNB (100 μM) plus TRX-S$_2$ (28 μM). As demonstrated in FIG. 5, diamide prevented elevation of MnSOD mRNA by thioredoxin. Thus, oxidized thioredoxin is incapable of inducing MnSOD in an oxidizing environment. Prior incubation of A549 cells with CDNB, a thiol alkylating agent, prevented increased expression of MnSOD mRNA by thioredoxin. This demonstrated that free thiol group(s) are necessary for MnSOD induction by thioredoxin.

Further support for a critical role for reduced thioredoxin is shown in this example, since diamide, a reversible thiol oxidizing agent, could inhibit MnSOD induction by thioredoxin. Since reduced thioredoxin was rapidly oxidized by diamide, the results demonstrated that oxidized thioredoxin is not capable of inducing MnSOD.

Example 4

The following example demonstrates a dose-response effect of thioredoxin on MnSOD expression.

Figure 6A:
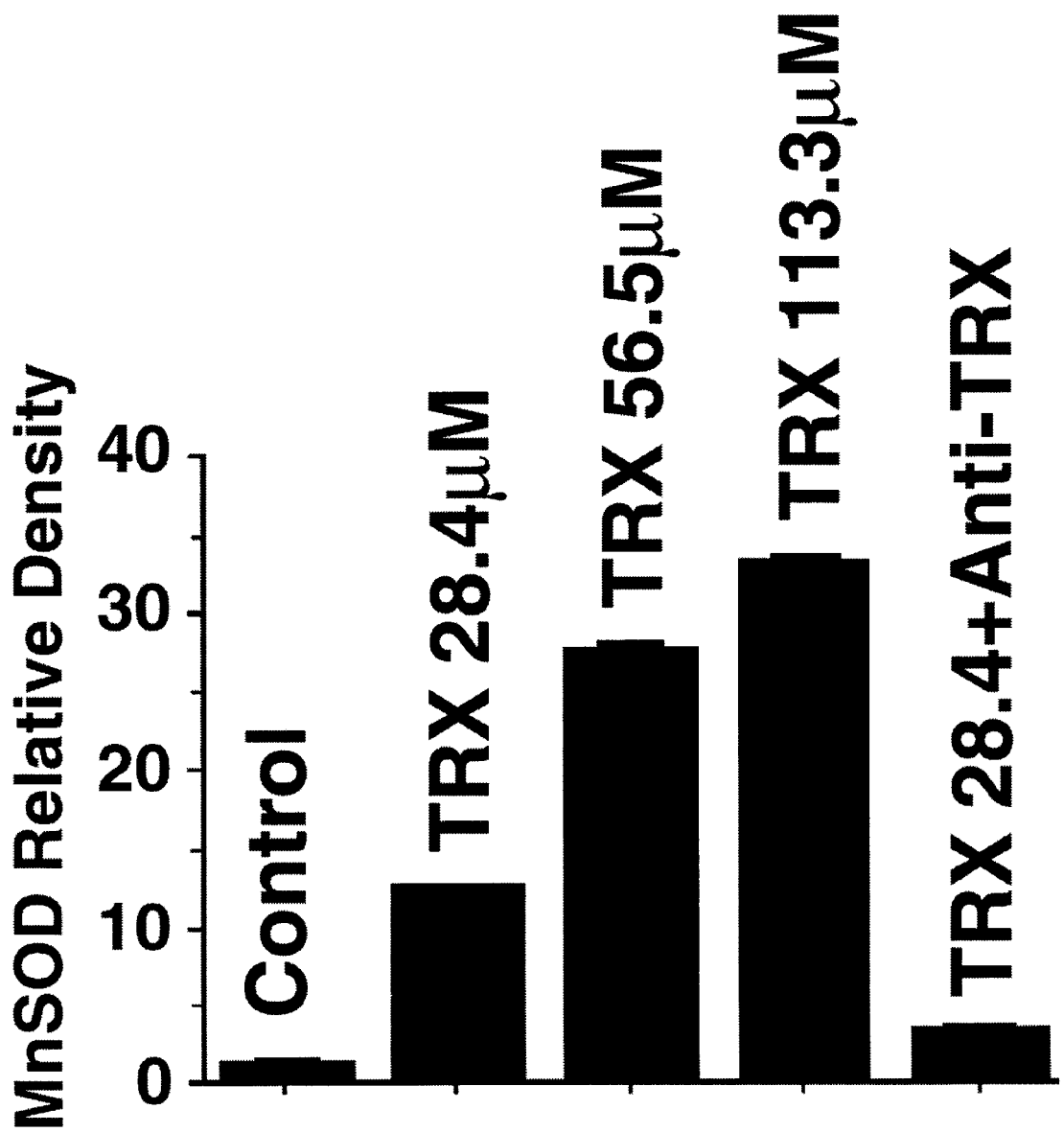
FIG. 6A demonstrates the effect of thioredoxin in reduced state on MnSOD induction.
Figure 6B:
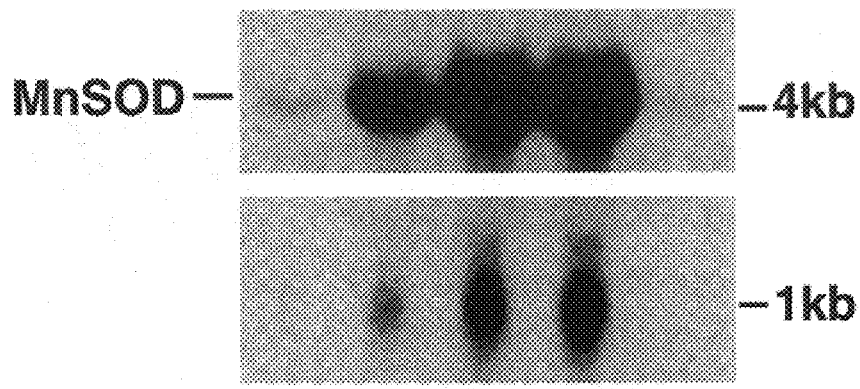
FIG. 6B demonstrates the effect of thioredoxin in reduced state on MnSOD induction.
Figure 6C:
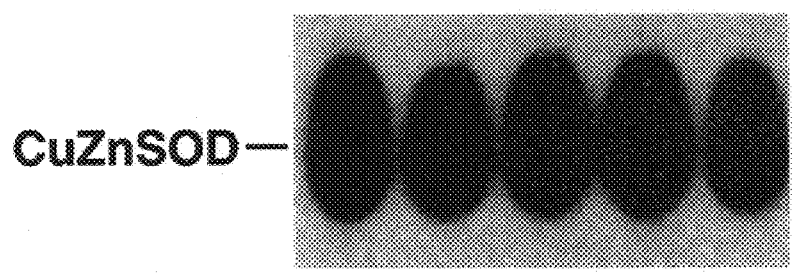
FIG. 6C demonstrates the effect of thioredoxin in reduced state on CuZnSOD induction.
Figure 6D:
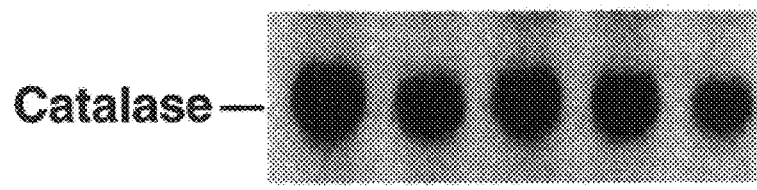
FIG. 6D demonstrates the effect of thioredoxin in reduced state on catalase mRNA induction.
Figure 6E:
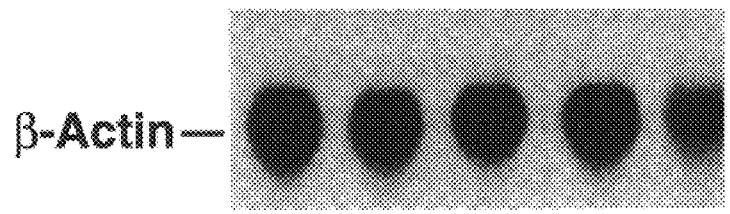
FIG. 6E demonstrates the effect of thioredoxin in reduced state on β-actin induction.

When human lung adenocarcinoma (A549) cells were incubated for 16 hours with various concentrations of thioredoxin (FIG. 6: 28 μM thioredoxin, lane 2; 56 μM thioredoxin, lane 3; and 113 μM thioredoxin, lane 4), significant elevation of steady-state MnSOD mRNA levels occurred in a dose-dependent manner (FIG. 6A: relative density of 1 kb band, mean±SEM, n=3 determinations per condition; FIG. 6B: relative density of 1 and 4 kb bands). This effect was specific for MnSOD because thioredoxin did not cause alteration in steady-state mRNA levels of other antioxidant enzymes such as copper-zinc superoxide dismutase (FIG. 6D) or catalase (FIG. 6C). In addition, there was no change in β-actin mRNA level (FIG. 6E).

To further determine the specificity of the thioredoxin-mediated increase in MnSOD mRNA, cells were incubated with antibody to thioredoxin (66 μg/ml) in addition to thioredoxin (28 μM)(lane 5). Elevation of MnSOD mRNA by thioredoxin was inhibited by this antibody (FIG. 6, lane 5).

Example 5

The following example shows the kinetics of induction of MnSOD at intervals following incubation with low concentrations (28 μM) of thioredoxin.

Figure 7:
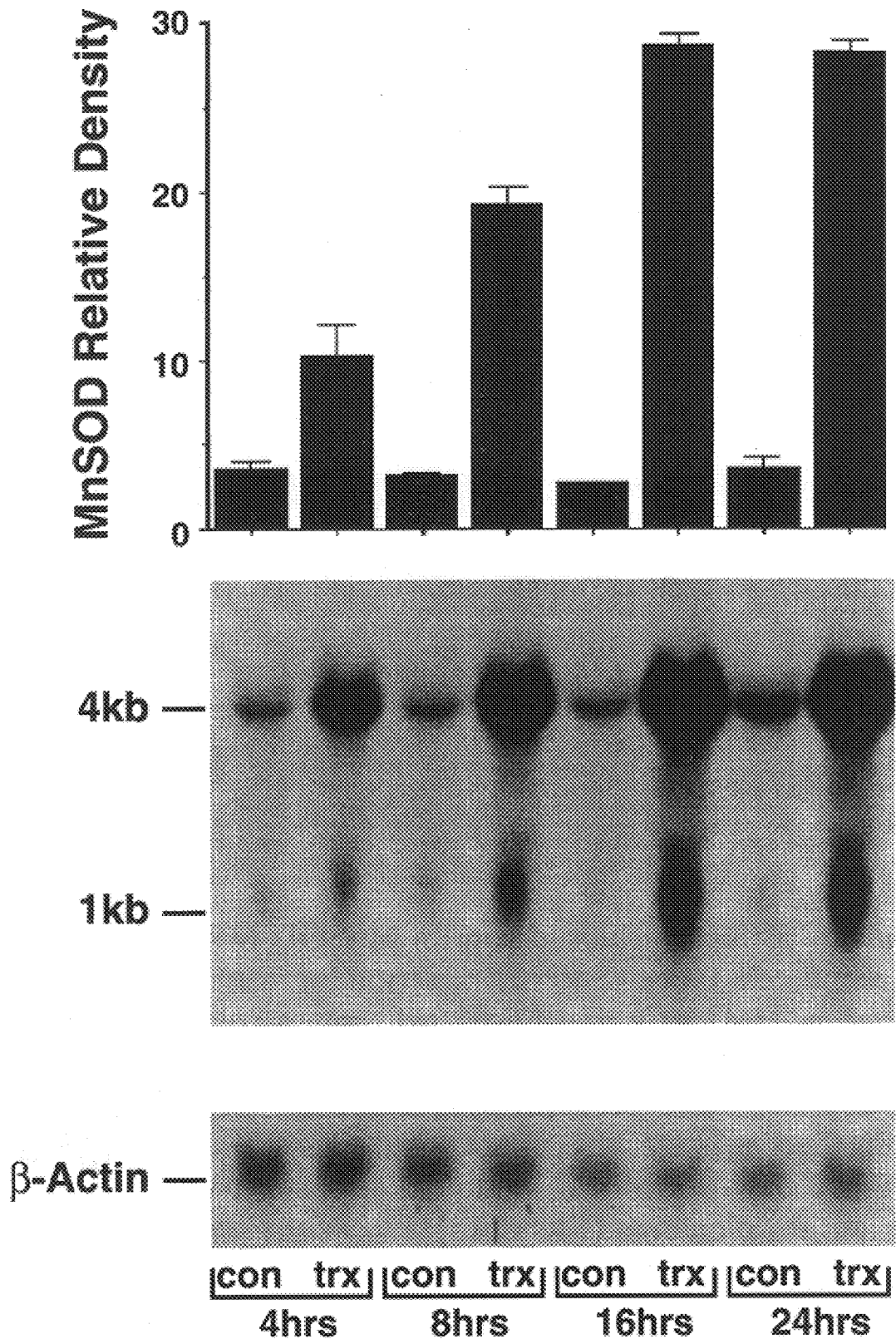
FIG. 7 illustrates the time course of MnSOD mRNA induction by thioredoxin in reduced state.

A549 cells were incubated with thioredoxin (28 μM) for 4, 8, 16 and 24 hours. mRNA was quantified as previously described. FIG. 7 shows the autoradiograph (data are mean±SEM; n=3 determinations per condition). A significant increase in MnSOD mRNA occurred after 16 and 24 hours (lanes 4 and 5) relative to control cells (lane 1). There was no significant difference in level of MnSOD mRNA at 16 relative to 24 hours (lanes 4 and 5). A maximal increase was observed after 16–24 hours. At this time, thioredoxin increased the level of MnSOD mRNA more than 15-fold. There was no alteration in the levels of β-actin mRNA.

Example 6

The following example shows the effect of actinomycin D and cycloheximide on induction of MnSOD mRNA.

Figure 8:
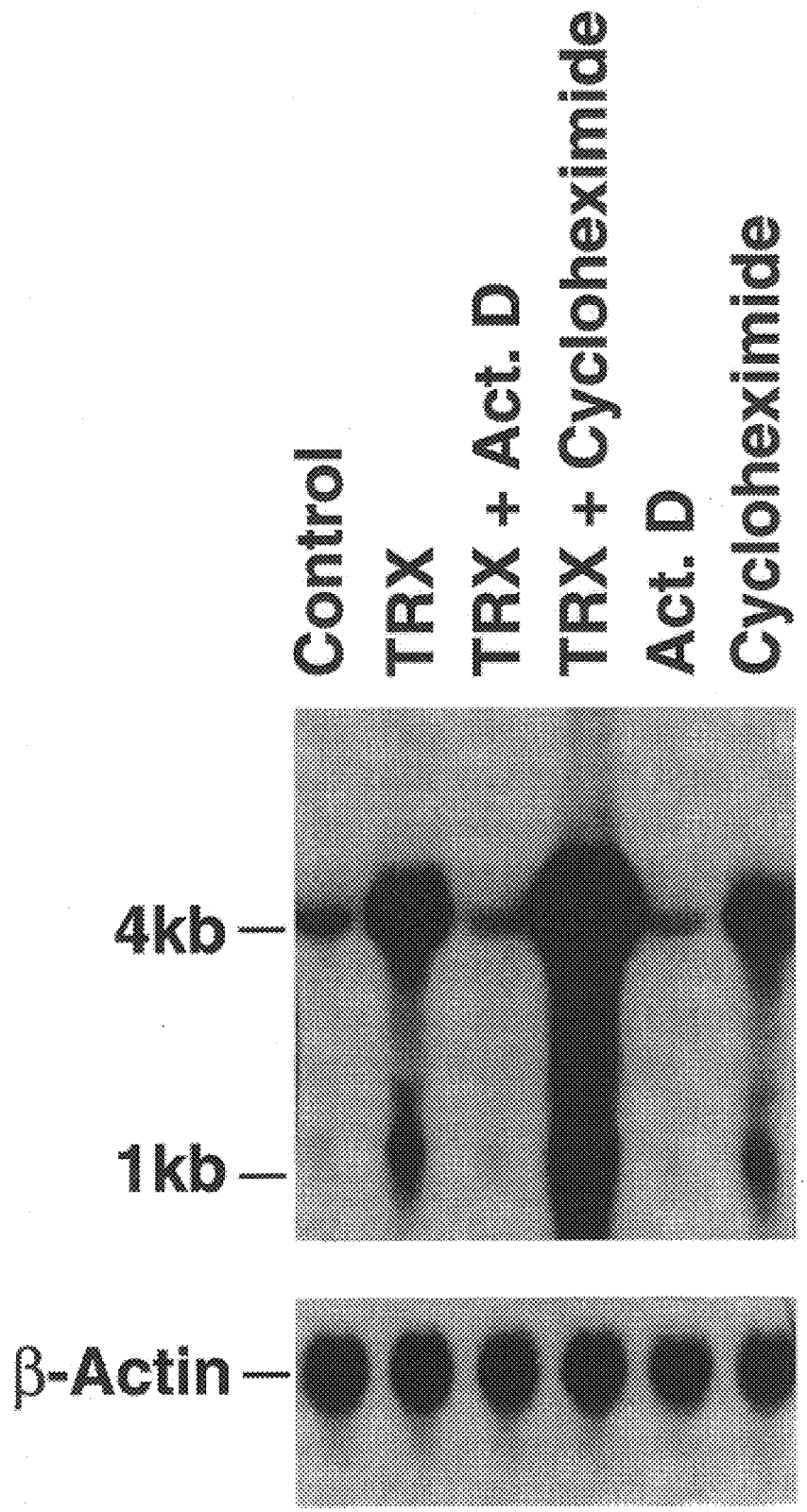
FIG. 8 shows the effect of a transcription inhibitor, actinomycin D, and a translation inhibitor, cycloheximide, on induction of MnSOD mRNA by thioredoxin in reduced state.

A549 cells were incubated with actinomycin D (100 mg/ml), a transcriptional inhibitor, or cyclohexamide (10 μg/ml), a translation inhibitor, for 1 hour followed by addition of thioredoxin (28 μM) and further incubation for a period of 16 hours. mRNA was quantified as previously described. FIG. 8 shows that production of MnSOD mRNA by A549 cells incubated with actinomycin D was inhibited, suggesting that the effect of thioredoxin occurs at the level of transcription. Cycloheximide potentiated the thioredoxin-mediated increase in MnSOD mRNA (lane 4). This result could be due to increased accumulation of mRNA in the absence of translation.

Example 7

This example demonstrates the effect of thioredoxin on MnSOD mRNA in different cell types.

To determine whether a similar increase of MnSOD occurs in cultures of other cell types, human lung microvascular endothelial cells in primary culture (HMVEC) were grown in endothelial basal medium along with nutrient supplements (Clonetics), mouse fibroblasts (L929) were grown in Dulbecco's Modified Eagle Medium, monkey kidney cells (OMK) were grown in RPMI 1640 media, and rat lung epithelial cells (L2) were grown in F-1 2K media. All media were supplemented with 10% fetal calf serum. Confluent monolayers were treated with thioredoxin (28 $\mu$M) and incubated for 16 hours. Following incubation mRNA was quantitated as previously described.

Figure 9:
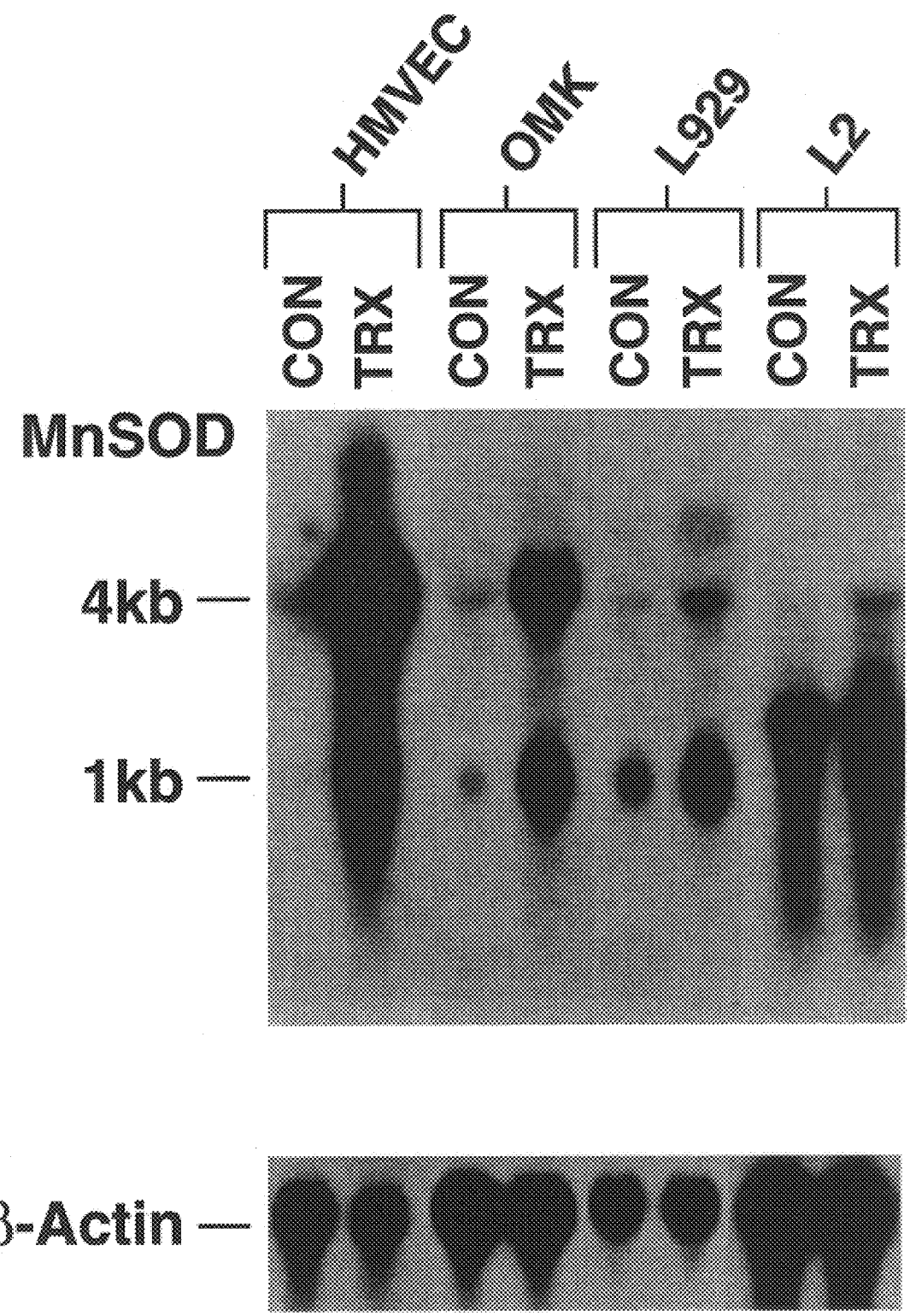
FIG. 9 illustrates the effect of thioredoxin in reduced state on MnSOD mRNA induction in various cell types.

MnSOD mRNA was elevated by thioredoxin exposure in each cell type tested (FIG. 9). Potent induction of MnSOD mRNA occurred in human lung microvascular endothelial cells (HMVEC) and monkey kidney (OMK) cells when treated with 28 $\mu$M thioredoxin (lanes 2 and 4). MnSOD mRNA also was induced by 28 $\mu$M thioredoxin in L929 and L2 cells. This induction (lanes 6 and 8) was diminished relative to primate cell lines. Therefore, the effect of thioredoxin was greater in cells of primates, such as those of humans and monkeys, than in rodent cells.

Example 8

The following example shows the effect of thioredoxin on MnSOD activity.

Because an increase in MnSOD enzyme activity confers protection against superoxide radical, the effect of thioredoxin on MnSOD activity was evaluated (FIG. 10).

To measure MnSOD activity after incubation of cells with thioredoxin, cells were sonicated (Braun-Sonic 2000, B. Braun) in three 15 second bursts (40° C.). A competitive inhibition assay was performed using hypoxanthine-xanthine oxidase generated $O_2$ to reduce nitroblue tetrazollium (NBT) monitored spectrophotometrically at 560 nm. Inhibition of NBT reduction to 50% of maximal is defined as 1 unit of SOD activity. Inhibition of CuZnSOD activity by 5 mM potassium cyanide allowed differentiation of CuZn-SOD and MnSOD. Protein concentrations were determined by Bradford assay (Bio-rad) and enzyme activity was expressed in units per milligram of protein. Data in FIG. 10 are mean±SEM (n=3 determinations per condition).

Figures 10A, 10B:
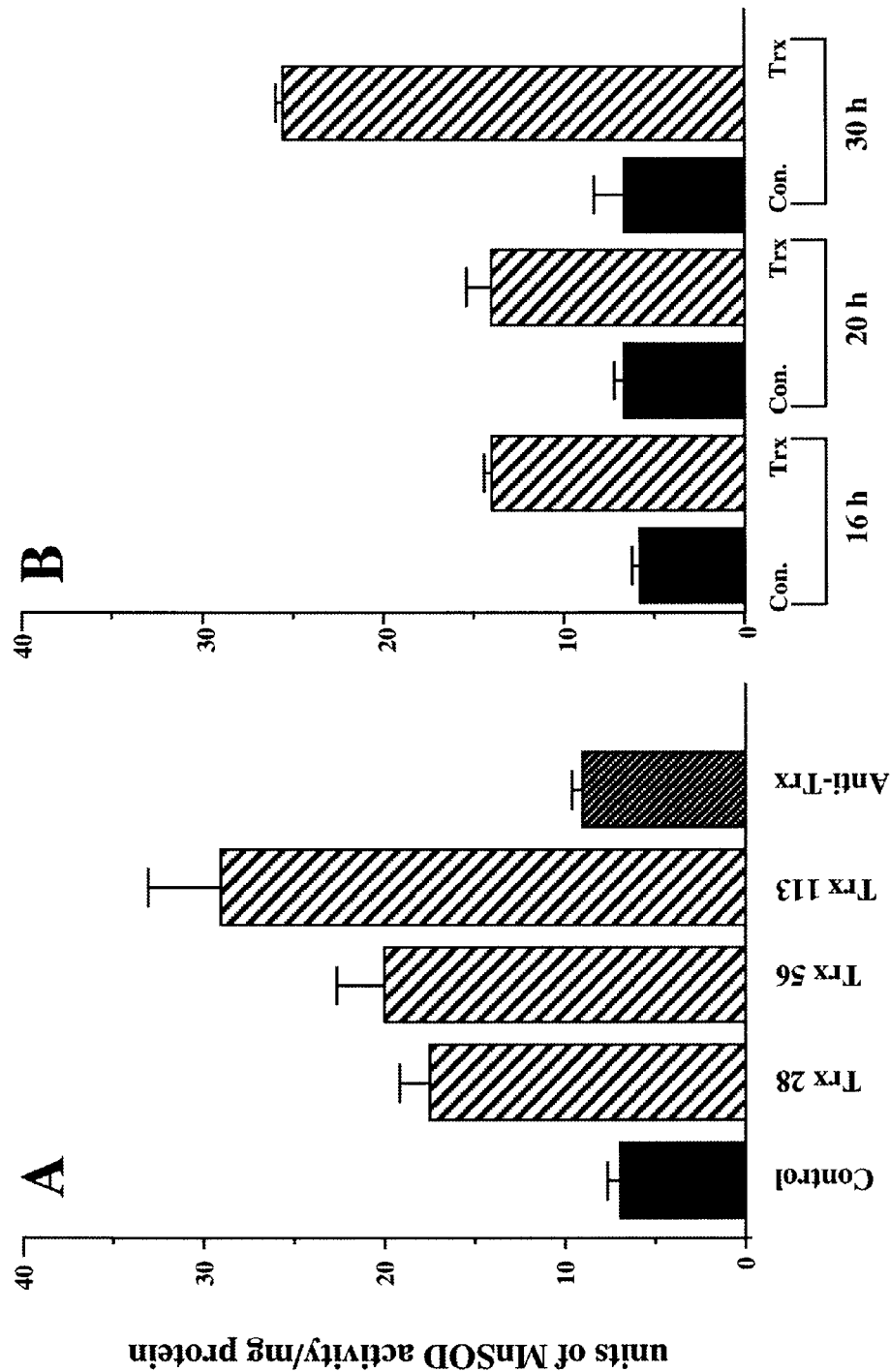
FIG. 10A shows the dose response of MnSOD enzyme activity induced by thioredoxin in reduced state.
FIG. 10B shows the time course of MnSOD enzyme activity induced by thioredoxin in reduced state.

Cells were incubated for 16 hours with thioredoxin (FIG. 10A: 28 $\mu$M, lane 2; 56 $\mu$M, lane 3; 113 $\mu$M, lane 4) or with thioredoxin (28 $\mu$M)+antibody to thioredoxin (FIG. 10A: 66 $\mu$g/ml, lane 5). MnSOD activities were measured. MnSOD activities increased significantly with increasing concentrations of thioredoxin. Addition of anti-thioredoxin antibody with thioredoxin (28 $\mu$M) inhibited the increase in MnSOD activity.

FIG. 10B shows the time course of increase in MnSOD activity. A549 cells were incubated with thioredoxin (28 $\mu$M) for 16 (lane 2), 20 (lane 4) and 30 (lane 8) hours. MnSOD activity was increased in a time dependent manner with maximal elevation after 30 hours.

In the present examples, the inventors have shown that MnSOD mRNA was strongly induced by reduced thioredoxin. Thioredoxin did not increase expression of other antioxidant enzymes such as catalase or CuZnSOD. Antibody to thioredoxin completely inhibited the induction of MnSOD mRNA by thioredoxin. These results demonstrate that the elevation of MnSOD mRNA by thioredoxin is specific and is both dose- and time-dependent. MnSOD mRNA was elevated in a variety of cell types in response to incubation with thioredoxin. This indicates that induction of MnSOD by thioredoxin is a generalized phenomenon. Inhibition of MnSOD induction by actinomycin D suggests that the thioredoxin effect occurs at the level of transcription.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:5 submitted herewith are the same.

SEQUENCE LISTING

```
(1) GENERAL INFORMATION:

(iii) NUMBER OF SEQUENCES: 5

(2) INFORMATION FOR SEQ ID NO:1:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (xi) SEQUENCE DESCRIPTION: SEQ ID NO:1:

Cys Xaa Xaa Cys
1

(2) INFORMATION FOR SEQ ID NO:2:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (xi) SEQUENCE DESCRIPTION: SEQ ID NO:2:
```

-continued

```
Cys Gly Pro Cys
1

(2) INFORMATION FOR SEQ ID NO:3:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:3:

Xaa Cys Xaa Xaa Cys Xaa
1               5

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:4:

Xaa Cys Gly Pro Cys Xaa
1               5

(2) INFORMATION FOR SEQ ID NO:5:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:5:

Trp Cys Gly Pro Cys Lys
1               5
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to increase a cellular level of manganese superoxide dismutase (MnSOD) in an animal to treat oxidative damage associated with a lung disease, comprising administering to lung tissue of said animal an amount of a protein containing a thioredoxin active-site in reduced state effective to induce the production of MnSOD.

2. The method of claim 1, wherein said lung disease is selected from the group consisting of infant respiratory distress syndrome, adult respiratory distress syndrome, interstitial lung disease, and asthma.

3. The method of claim 1, wherein said protein is administered by at least one route selected from the group consisting of nasal, intratracheal and inhaled routes.

4. The method of claim 1, wherein said protein is administered in a pharmaceutically acceptable delivery vehicle.

5. The method of claim 1, wherein said protein is administered in an amount that is between about 1.5 mmoles/kg and about 150 mmoles/kg.

6. The method of claim 1, wherein said protein is administered in an amount that is between about 2 mmoles/kg and about 25 mmoles/kg.

7. The method of claim 1, wherein said protein is administered in an amount that is between about 3 mmoles/kg and about 10 mmoles/kg.

8. The method of claim 1, wherein said protein has a half-life in said animal of between about 5 minutes and about 24 hours.

9. The method of claim 1, wherein said protein has a half-life in said animal of between about 2 hours and about 16 hours.

10. The method of claim 1, wherein said protein has a half-life in said animal of between about 4 hours and about 12 hours.

11. The method of claim 1, wherein said cellular level of MnSOD is increased at least about 2-fold.

12. The method of claim 1, wherein said cellular level of MnSOD is increased at least about 5-fold.

13. The method of claim 1, wherein said cellular level of MnSOD is increased at least about 10-fold.

14. The method of claim 1, wherein said thioredoxin active-site comprises the amino acid sequence C-X-X-C (SEQ ID NO:1), wherein C residues are in reduced state, and wherein X residues are any amino acid residue.

15. The method of claim 1, wherein said thioredoxin active-site comprises the amino acid sequence X-C-X-X-C-X (SEQ ID NO:3), wherein C residues are in reduced state, and wherein X residues are any amino acid residue.

16. The method of claim 1, wherein said thioredoxin active-site comprises the amino acid sequence X-C-G-P-C-X (SEQ ID NO:4), wherein C residues are in reduced state, and wherein X residues are any amino acid residue.

17. The method of claim 1, wherein said thioredoxin active-site comprises the amino acid sequence W-C-G-P-C-K (SEQ ID NO:5), wherein C residues are in reduced state.

18. The method of claim 1, wherein said protein comprises thioredoxin selected from the group consisting of prokaryotic thioredoxin, yeast thioredoxin and mammalian thioredoxin.

19. The method of claim 1, wherein said protein comprises human thioredoxin.

20. The method of claim 1, wherein said animal is a mammal.

21. The method of claim 20, wherein said mammal is a human.

22. A composition for increasing a cellular level of MnSOD in an animal to treat oxidative damage associated with a lung disease, comprising a protein containing a thioredoxin active-site in reduced state effective to induce the production of MnSOD, formulated with a pharmaceutically acceptable delivery vehicle selected from the group consisting of liposomes, liposheres and surfactants, which provides a half-life of between about 5 minutes and about 24 hours in said animal.

23. The composition of claim 22, wherein said thioredoxin active-site comprises the amino acid sequence C-X-X-C (SEQ ID NO:1), wherein C residues are in reduced state, and wherein said X residues are any amino acid residue.

24. The composition of claim 22, wherein said thioredoxin active-site comprises the amino acid sequence X-C-X-X-C-X (SEQ ID NO:3), wherein C residues are in reduced state, and wherein said X residues are any amino acid residue.

25. The composition of claim 22, wherein said thioredoxin active-site comprises the amino acid sequence X-C-G-P-C-X (SEQ ID NO:4), wherein C residues are in reduced state, and wherein said X residues are any amino acid residue.

26. The composition of claim 22, wherein said thioredoxin active-site comprises the amino acid sequence W-C-G-P-C-K (SEQ ID NO:5), wherein C residues are in reduced state.

27. The composition of claim 22, wherein said formulation further comprises about 0.1 unit/liter achieved surface concentration of thioredoxin reductase and about 1 mM achieved surface concentration of nicotinamide-adenine dinucleotide phosphate (reduced form) (NADPH).

28. The composition of claim 22, wherein said protein comprises thioredoxin selected from a group consisting of prokaryotic thioredoxin, yeast thioredoxin and mammalian thioredoxin.

29. The composition of claim 22, wherein said protein comprises human thioredoxin.

30. A method to treat an animal from cellular injury due to oxidative damage associated with a lung disease by increasing a cellular level of manganese superoxide dismutase (MnSOD), comprising administering to lung tissue of said animal a protein comprising the amino acid sequence X-C-X-X-C-X (SEQ ID NO:3), wherein C residues are in reduced state, effective to induce the production of MnSOD.

31. The method of claim 30, wherein said protein comprises the amino acid sequence X-C-G-P-C-X (SEQ ID NO:4).

32. The method of claim 30, wherein said protein comprises the amino acid sequence W-C-G-P-C-K (SEQ ID NO:5).

33. The method of claim 30, wherein said protein has a half-life in the animal of between about 5 minutes and about 24 hours.

34. The method of claim 30, wherein said protein is administered in an amount that is between about 1.5 mmoles/kg and about 150 mmoles/kg.

35. The method of claim 30, wherein said protein comprises thioredoxin selected from a group consisting of prokaryotic thioredoxin, yeast thioredoxin and mammalian thioredoxin.

36. The method of claim 30, wherein said lung disease is selected from the group consisting of infant respiratory distress syndrome, adult respiratory distress syndrome, interstitial lung disease, and asthma.

37. The method of claim 30, wherein said animal is a human.

* * * * *